United States Patent [19]

Sonawane et al.

[11] Patent Number: 4,906,343

[45] Date of Patent: Mar. 6, 1990

[54] PROCESS FOR THE PHOTOCHEMICAL PRODUCTION OF α-ARYL PROPIONIC ACID

[76] Inventors: Harikisan R. Sonawane; Dilip G. Kulkarni; Nagaraj R. Ayyangar, all of c/o. National Chemical Laboratory, Pune, Maharashtra, India

[21] Appl. No.: 181,194

[22] Filed: Apr. 13, 1988

[51] Int. Cl.$^4$ ............................................. B01J 19/08
[52] U.S. Cl. ........................... 204/157.87; 204/157.88; 204/157.89
[58] Field of Search ...................... 204/157.87, 157.88, 204/157.89, 157.92, 157.93, 157.96, 157.97, 157.98, 157.99, 158.1

[56] References Cited

U.S. PATENT DOCUMENTS 3,907,878 9/1975 Houlihan ..................... 204/157.93

Primary Examiner—John F. Niebling
Assistant Examiner—Ben C. Hsing
Attorney, Agent, or Firm—Ladas & Parry

[57] ABSTRACT

The invention resides in a novel photochemical process for the production of α-aryl propionic acids by the subjection of a solution in an organic solvent of the corresponding α-haloaryl alkyl ketones to irradiation with light having a wavelength of from 200 to 800 nm, preferably in the presence of a suitable acid scavenger for the neutralization of any hydrohalogen acid generated during the reaction.

11 Claims, No Drawings

PROCESS FOR THE PHOTOCHEMICAL PRODUCTION OF α-ARYL PROPIONIC ACID

BACKGROUND OF THE INVENTION

The present invention relates to an improved process for the preparation of α-aryl propionic acids by the photochemical reaction of haloalkyl aryl ketones. α-aryl propionic acids are useful as anti-inflamatory, antipyretic and analgesic agents.

The preparation of α-aryl propionic acids has so far followed the so-called classic chemical methods which employ as starting material aryl alkyl ketone derivatives and are known by such names as Darzen's reaction, Willgerodt's reaction, Arndt-Eistert's reaction and Friedel-Crafts reaction. Of these, Darzen's reaction constitutes more or less the generally accepted basic method for the preparation of α-aryl propionic acids. This method comprises the reaction of aryl alkyl ketones with alkyl chloroacetate in the presence of alkali metal alkoxides in an alcoholic solvent. [D. R. White (The Upjohn Company) U.S. Pat. No. 3,975,431 (1976); Chemical Abstracts 86,5168 w].

An alternative method for the preparation of α-aryl propionic acids involves the alkaline hydrolysis of α-aryl propionitrile or its derivatives [N. Tokutake (Shionogi and Company Limited), Japanese Pat. No. 77,111,536 (1977); Chemical Abstracts 88: 50512f].

Other prior art methods include the chemical rearrangement of α-haloalkyl aryl ketones in the presence of Lewis acids [Claudio Giordao, Graziano Castaldi & Fulvio Uggeri, Agnewandte Chemie, International Edition, English, 23 (1984) 413–419 ]; the α-alkylation of aryl acetic esters or aryl acetonitriles [W. G. Kenyon, R. B. Meyer and C. R. Hauser, Journal of Organic Chemistry, 28(11), 3108 (1963)]; and "Research on biphenyl, stilbene and diphenylethane derivatives" [G. Cavallini, E. Massarani, D. Nardi and R. D'Ambrosio, Journal of the American Chemical Society, 79, 3514 (1957)].

More recently, newer methods have been proposed for the preparation of α-aryl propionic acids. These include Gassman's procedure and vicarious neucleophilic substitution and chemical re-arrangement of propionic acid derivatives [P.G. Gassman and T. J. Van Bergen, Journal of the Americal Chemicals Society, 96(17), 5508 (1974); G. P. Stahly, B. C. Stahly and K. C. Lilge, Journal of Organic Chemistry, 49 579 (1984); M. S. Newman and B. J. Magertein, Organic Reactants V, 413 (1949); Brown, E. V. Synthesis, 358 (1975); S. Yoshimura, S. Takahashi and M. Ichino (Kohjin Company), Japanese Pat. No. 76,36,432 (Mar. 27, 1976); and Chemical Abstract 85,123596 m].

While the prior art processes suffer from a few minor drawbacks, there is one major disadvantage which is common to all of them and that is the multiplicity of reactions and the overall length of time taken. In almost every instance, a number of reaction steps involving lengthy sequences of introduction of reactants are involved. Such reactants include alkyl or carboxylic ester groups with suitable precursors. Frequently, such steps take from 12 to 24 hours and the overall time for recovery of the final product is even longer.

The lesser drawbacks of the prior art processes include the employment of toxic reactants such as sodium cyanide, the use of relatively expensive materials such as isopropyl monochloroacetates and the difficulty of reproducing the reactions for a large scale operation without leading to the formation of a number of undesirable by-products.

The principal object of the present invention is to provide a process for the preparation of α-aryl propionic acids which does away with the essential drawback of multiplicity of steps and overall length of time of the reaction endemic in the prior art.

A more specific object resides in the provision of a one-step process for the preparation of α-aryl propionic acids employing easily obtainable starting products and which avoids the use of expensive or hazardous raw materials for the reaction.

Towards achieving their objective, the applicants have researched the area of photochemistry and have been able to establish that it is possible to obtain the desired α-aryl propionic acids in a single step treatment by subjecting a haloalkyl aryl ketone to irradiation with light of a particular wavelength.

Accordingly, the present invention provides a process for the photochemical production of α-aryl propionic acids of the general formula:

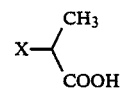

wherein X is a radical of the structure:

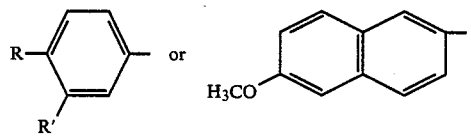

wherein R is hydrogen, methyl, ethyl, n-propyl, isopropyl, n-butyl, sec-butyl, isobutyl, tert-butyl, n-amyl, isoamyl, chloro, methoxy or phenyl and R¹ is hydrogen or halogen which comprises subjecting an -haloaryl alkyl ketone of the general formula:

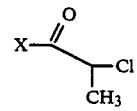

wherein X has the meanings stated above to irradiation with light having a wavelength of from 200 to 800 nm in the presence of an anhydrous or aqueous organic solvent at a temperature from 0° C. to the boiling point of the solvent.

The light employed for irradiation can be either sunlight or artificial light, for instance the light of a mercury vapour lamp.

Effectively, the reaction is carried out over a period of from 1.5 to 20 hours.

In accordance with a preferred feature of the invention, esters of α-aryl propionic acids formed during the photocohemical reaction are hydrolysed in situ by means of aqueous alkali to provide the corresponding acids.

Examples of the ketones that may be employed as starting materials in the process of the present invention include α-chloropropionphenone, α-chloro-1-(4'-chlorophenyl)-1-propanone, α-chloro-1-(4'-methylphenyl)-propanone, α-chloro-1-(4'-isobutylphenyl)-1- propanone, α-chloro-1-(4'-methoxyphenyl)-1-propanone and 2-chloro-1-(4'-methoxyphenyl)-1-propanone.

A particularly preferred ketone is (6-methoxy-2-naphthyl)-α-chloroethyl ketone of the formula:

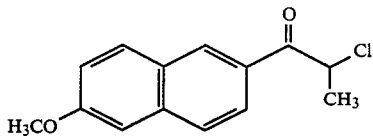

Subjection of this ketone to irradiation of the intensity described above in the presence of the stated solvents converts it to the corresponding α-(6-methoxy-2-naphyhyl)-propionic acid of the formula:

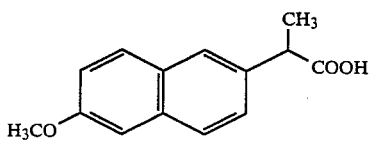

Preferred solvents for the reaction include acetone, methyl alcohol, ethyl alcohol, acetonitrile and tetrahydrofuran.

The reaction according to the invention for the conversion under the influence of light irradiation of α-halo aryl alkyl ketones to α-aryl propionic acids generates simultaneously equimolar amounts of hydrohalogen acid such as hydrochloric acid. It therefore becomes necessary to neutralise the hydrohalogen acid produced.

According to a further feature of the invention, therefore, a suitable acid scavenger is incorporated into the solution of solvent and α-aryl alkyl ketone prior to irradiation thereof. Since the reaction liberates hydrohalogen acid in molar proportions, it becomes necessary to employ the scavengers in equivalent amounts.

Examples of suitable acid scavengers that can be employed with the process of the present invention include potassium carbonate, epichlorohydrin, triethylamine and propylene oxide.

The invention will now be illustrated in greater detail in the following examples.

EXAMPLE 1

A solution comprising 5 parts of α-chloropropiophenone and 3 parts of anyhydrous potassium carbonate in 300 parts of anhydrous methyl alcohol was irradiated by means of a medium pressure 200W mercury vapour lamp for 6 hours at 30° C. The solvent was removed by distillation and the resulting methyl ester of α-phenyl propionic acid was treated with 10% w/v aqueous alcoholic sodium hydroxide at 100° C. for 3 hours to effect hydrolysis and thereby to yield 3.2 parts of α-phenyl propionic acid b.p. 125° C. at 20 mm mercury.

EXAMPLE 2

A solution comprising 5 parts of α-chloropropiophenone and 5 parts of epichlorohydrin in 300 parts of 10% v/v aqueous acetone was irradiated by means of a medium pressure 200W mercury vapour lamp for 5 hours at 25° C. The solvent was removed by distillation and the resulting acid was extracted with 5% w/v aqueous sodium hydroxide. Acidification with dilute sulphuric acid (10% v/v) yielded 2.2 parts α-phenyl propionic acid, b.p. 25° C. at 20 mm mercury.

EXAMPLE 3

A solution comprising 10 parts of α-chloro-1-(4'-chlorophenyl)-1-propanone and 10 parts of epichlorohydrin in 650 parts of anhydrous ethyl alcohol was irradiated by means of a 400W mercury vapour lamp for 4 hours at 28° C. The solvent was removed by distillation and the resulting ethyl ester was saponified by refluxing it with 10% w/v aqueous alcoholic sodium hydroxide for 2.5 hours at 100° C. to yield on acidification 6.2 parts of α-(4-chlorophenyl)-propionic acid m.p. 54° C. to 56° C.

EXAMPLE 4

A solution comprising 10 parts of α-chloro-1-(4'-methylphenyl)-propanone and 6 parts of triethylamine in 300 parts of 10% v/v aqueous tetrahydrofuran was irradiated by means of a 200W mercury vapour lamp for 8 hours at 30° C. The solvent was removed by distillation and the resulting acid was extracted with dilute 5% w/v sodium hydroxide which on acidification yielded 6.4 parts of α-(4'-methylphenyl)-propionic acid, m.p. 37° C. to 39° C.

EXAMPLE 5

A solution comprising 10 parts of α-chloro-1-(4'-isobutylphenyl)-1-propanone and 10 parts of epichlorohydrin in 300 parts of aqueous acetone was placed in a long tubular reactor in direct sunlight for 10 hours. The solvent was removed by distillation and the resulting acid was extracted with dilute 5% w/v sodium hydroxide solution which on acidification yielded 7 parts of α-(4'-isobutylphenyl)-propionic acid, m.p. 75° C. to 77° C.

EXAMPLE 6

A solution comprising 8 parts of α-chloro-1-(4'-methoxyphenyl)-1-propanone and 7 parts of epichlorohydrin in 300 parts of 10% v/v aqueous acetonitrile was irradiated by means of a 200W mercury lamp for 7 hours. The solvent was removed by distillation and the resulting acid on extraction with 5% w/v aqueous sodium hydroxide followed by acidification 10% v/v dilute sulphuric acid to yield 5 parts of α-(4'-methoxyphenyl)-propionic acid, m.p. 55° C. to 56° C.

EXAMPLE 7

A solution comprising 5 parts of α-chloro-1-(4'-isobutylphenyl)-1-propanone and 4 parts of epichlorohydrin in 300 parts of 10% v/v aqueous ethyl alcohol was irradiated by means of a 450W mercury vapour lamp for 3 hours to give a mixture of free acid and ethyl ester of α-(4'-isobutylphenyl)-propionic acid. The solvent was removed by distillation and the mixture of acid and ethyl ester was refluxed with 10% w/v aqueous alcoholic sodium hydroxide for 3 hours to yield on acidification 3.2 parts of α-(4'-isobutylphenylphenyl)-propionic acid, m.p. 76° C. to 77° C.

EXAMPLE 8

A solution comprising 10 parts of α-chloro-1-(4'-chlorophenyl)-1-propanone and 5 parts of anhydrous potassium carbonate in 300 parts of anhydrous methyl alcohol was irradiated by means of a 200W mercury vapour lamp for 8 hours. The solvent was removed by distillation and the resulting methyl ester was saponified with 10% w/v aqueous alcoholic sodium hydroxide for 3 hours at 100° C. to provide on acidification 5.7 parts of α-(4'-chlorophenyl)-propionic acid, m.p. 55° C. to 56° C.

EXAMPLE 9

A solution comprising 15 parts of α-chloro-1-(4'-isobutylphenyl)-1-propanone and 600 parts of anhydrous methyl alcohol was irradiated by means of a 200W mercury vapour lamp for 7 hours. The solvent was removed by distillation and the resulting methyl ester was saponified with 10% w/v sodium hydroxide for 3 hours at 100° C. to yield on acidification 9 parts of α-(4-isobutylphenyl)-propionic acid, m.p. 75° C. to 76° C.

EXAMPLE 10

A solution comprising 15 parts of 2-chloro-1-(4'-methoxyphenyl)-1-propanone and 10 parts of propylene oxide in 500 parts of 10% v/v aqueous acetone was irradiated by means of a 450W mercury vapour lamp for 8 hours. The solvent was removed by distillation and the resulting acid was extracted with 5% w/v aqueous sodium hydroxide. Acidification yielded 9.5 parts of α-(4'-methoxyphenyl)-propionic acid, m.p. 55° C. to 57° C.

EXAMPLE 11

A solution comprising 8 parts of α-chloro-1-(4'-methylphenyl)-1-propanone and 3 parts of triethylamine in 300 parts of ethyl alcohol was placed in a glass reactor in direct sunlight for 14 hours. The resulting ethyl ester was saponified after removing the solvent by distillation and refluxing the residue in 10% w/v aqueous alcoholic sodium hydroxide for 3 hours to yield 5 parts of α-(4'-methylphenyl)-propionic acid, m.p. 37° C. to 38° C.

The process of the present invention affords a number of advantages over the prior art. Chief among these is the process's obviation of the lengthy, time-consuming procedure hitherto employed for the protection of the carbonyl group of α-haloalkyl aryl ketones by the formation of acetals. By employing a single one-step process, the cost of production relative to the prior art processes is also considerably reduced.

Other advantages include the avoidance of the use of Lewis acids and their salts such as anhydrous zinc chloride and of expensive raw materials such as isopropyl monochloro acetates. The process does not bring with it problems of corrosion or handling hazards since it does not employ any toxic reactants.

On the position side, the process of the present invention employs extremely mild reaction conditions and its work-up procedures are simple. The product resulting from the process is of high purity of approximately 98% and is obtained in a high yield of about 90%.

We claim:

1. A process for the photochemical production of an α-aryl propionic acid of the general formula:

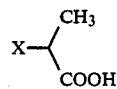

wherein X is a radical of the structure:

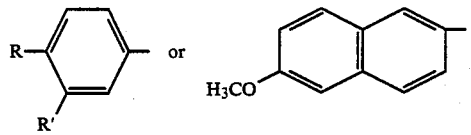

wherein R is selected from the group consisting of hydrogen, methyl, ethyl, n-propyl, isopropyl, n-butyl, sec-butyl, isobutyl, tert-butyl, n-amyl, isoamyl, chloro, methoxy and phenyl and R' is selected from the group consisting of hydrogen and halogen which comprises subjecting an α-haloaryl alkyl ketone of the general formula:

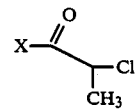

wherein X has the meanings stated above to irradiation with light having a wavelength of from 200 to 800 nm in the presence of an anhydrous or aqueous organic solvent at a temperature from 0° C. to the boiling point of the solvent.

2. A process as claimed in claim 1 wherein said light is sunlight or artificial light.

3. A process as claimed in claim 1 wherein said photochemical reaction is carried out over the period of from 1.5 to 20 hours.

4. A process as claimed in claim 1 wherein said photochemical reaction is effected at a temperature of from 25° C. to 30° C.

5. A process as claimed in claim 1 wherein the ketone subjected to irradiation is (6-methoxy-2-naphthyl)-chloroethyl ketone.

6. A process as claimed in claim 1 wherein any esters of α-aryl propionic acids formed during said photochemical reaction are hydrolysed in situ by means of aqueous alkali to provide the corresponding acids.

7. A process as claimed in claim 6 wherein said alkali is sodium hydroxide.

8. A process as claimed in claim 1 wherein the solvent for the reaction is selected from a group consisting of acetone, methyl alcohol, ethyl alcohol, acetonitrile and tetrahydrofuran.

9. A process as claimed in claim 1 wherein an acid scavenger is incorporated into a solution of solvent and α-haloaryl alkyl ketone prior to irradiation in order to neutralize any hydrohalogen acid liberated during the photochemical reaction.

10. A process as claimed in claim 9 wherein said acid scavenger is selected from a group consisting of potassium carbonate, epichlorohydrin, triethylamine and propylene oxide.

11. A process as claimed in claim 1 wherein said light is light from a mercury vapour lamp.

* * * * *